(12) United States Patent
Min et al.

(10) Patent No.: US 10,498,729 B2
(45) Date of Patent: Dec. 3, 2019

(54) DEVICE AND METHOD FOR TRANSMITTING MESSAGE

(71) Applicant: Samsung Electronics Co., Ltd., Suwon-si, Gyeonggi-do (KR)

(72) Inventors: Chan-hong Min, Yongin-si (KR); Sun-hwa Kim, Seoul (KR); Jin La, Suwon-si (KR); Jong-hyun Ryu, Suwon-si (KR); Kyung-ho Jeong, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 83 days.

(21) Appl. No.: 15/541,916

(22) PCT Filed: Jan. 5, 2016

(86) PCT No.: PCT/KR2016/000047
§ 371 (c)(1),
(2) Date: Jul. 6, 2017

(87) PCT Pub. No.: WO2016/111519
PCT Pub. Date: Jul. 14, 2016

(65) Prior Publication Data
US 2018/0026975 A1    Jan. 25, 2018

(30) Foreign Application Priority Data

Jan. 6, 2015   (KR) .......................... 10-2015-0001177

(51) Int. Cl.
*H04L 29/06* (2006.01)
*A61B 5/1171* (2016.01)
(Continued)

(52) U.S. Cl.
CPC .......... *H04L 63/0861* (2013.01); *A61B 5/117* (2013.01); *A61B 5/1171* (2016.02);
(Continued)

(58) Field of Classification Search
CPC ... H04L 63/0861; H04L 9/3231; H04L 51/18; H04L 67/025; H04L 67/125;
(Continued)

(56) References Cited

U.S. PATENT DOCUMENTS 7,480,805 B1 * 1/2009 Gnech .................... G06F 21/31
                                                  713/182
7,956,730 B2   6/2011 White et al.
(Continued)

FOREIGN PATENT DOCUMENTS

KR        10-0604582 B1   7/2006
KR      10-2008-0066134 A   7/2008
(Continued)

*Primary Examiner* — Ghodrat Jamshidi
(74) *Attorney, Agent, or Firm* — Jefferson IP Law, LLP

(57) ABSTRACT

Provided is a method of transmitting a message. The method includes: obtaining identification information used to identify a user based on bio information of the user that is obtained by a device; determining whether control over an external device is approved based on the identification information; obtaining control information used to control an operation of the external device based on the determination; and transmitting a message including the control information to the external device.

14 Claims, 10 Drawing Sheets

(51) Int. Cl.
  *A61B 5/117*   (2016.01)
  *A61B 5/1172*  (2016.01)
  *H04L 29/08*   (2006.01)
  *H04L 9/32*    (2006.01)
  *H04L 12/58*   (2006.01)

(52) U.S. Cl.
  CPC .......... *A61B 5/1172* (2013.01); *H04L 9/3231* (2013.01); *H04L 51/18* (2013.01); *H04L 67/025* (2013.01); *H04L 67/125* (2013.01); *H04L 2209/60* (2013.01); *H04L 2209/80* (2013.01)

(58) Field of Classification Search
  CPC ............. H04L 2209/60; H04L 2209/80; A61B 5/1171; A61B 5/117; A61B 5/1172
  See application file for complete search history.

(56) References Cited

U.S. PATENT DOCUMENTS

| | | | | |
|---|---|---|---|---|
| 8,275,992 | B2* | 9/2012 | Ushiku | G06F 21/32 713/166 |
| 9,209,652 | B2 | 12/2015 | Imes et al. | |
| 2004/0010327 | A1 | 1/2004 | Terashima et al. | |
| 2007/0112906 | A1* | 5/2007 | Liu | H04L 67/02 709/200 |
| 2008/0313470 | A1* | 12/2008 | Pall | G06F 21/32 713/183 |
| 2009/0022374 | A1* | 1/2009 | Boult | G06K 9/00885 382/119 |
| 2009/0164799 | A1* | 6/2009 | Takagi | G06Q 20/341 713/186 |
| 2009/0191846 | A1* | 7/2009 | Shi | G06F 21/32 455/411 |
| 2009/0282258 | A1* | 11/2009 | Burke | G06F 21/31 713/184 |
| 2010/0045423 | A1* | 2/2010 | Glickman | G06Q 10/087 340/5.1 |
| 2011/0055277 | A1* | 3/2011 | Resch | G06F 11/1004 707/785 |
| 2011/0238573 | A1* | 9/2011 | Varadarajan | G06Q 20/1085 705/43 |
| 2012/0079581 | A1* | 3/2012 | Patterson | G06Q 20/206 726/7 |
| 2012/0159599 | A1* | 6/2012 | Szoke | G06F 21/32 726/7 |
| 2014/0082501 | A1 | 3/2014 | Bae et al. | |
| 2015/0242601 | A1* | 8/2015 | Griffiths | G06F 21/305 726/5 |
| 2015/0242605 | A1* | 8/2015 | Du | G06F 21/32 726/7 |
| 2015/0317855 | A1* | 11/2015 | Sezan | A61B 5/1171 340/5.52 |
| 2016/0094550 | A1* | 3/2016 | Bradley | H04W 4/80 726/7 |
| 2017/0109751 | A1* | 4/2017 | Dunkelberger | H04L 9/3226 |

FOREIGN PATENT DOCUMENTS

| | | |
|---|---|---|
| KR | 10-2008-0106244 A | 12/2008 |
| KR | 10-2012-0043848 A | 5/2012 |
| KR | 10-2012-0087887 A | 8/2012 |
| KR | 10-2014-0039961 A | 4/2014 |
| KR | 10-2014-0140818 A | 12/2014 |

* cited by examiner

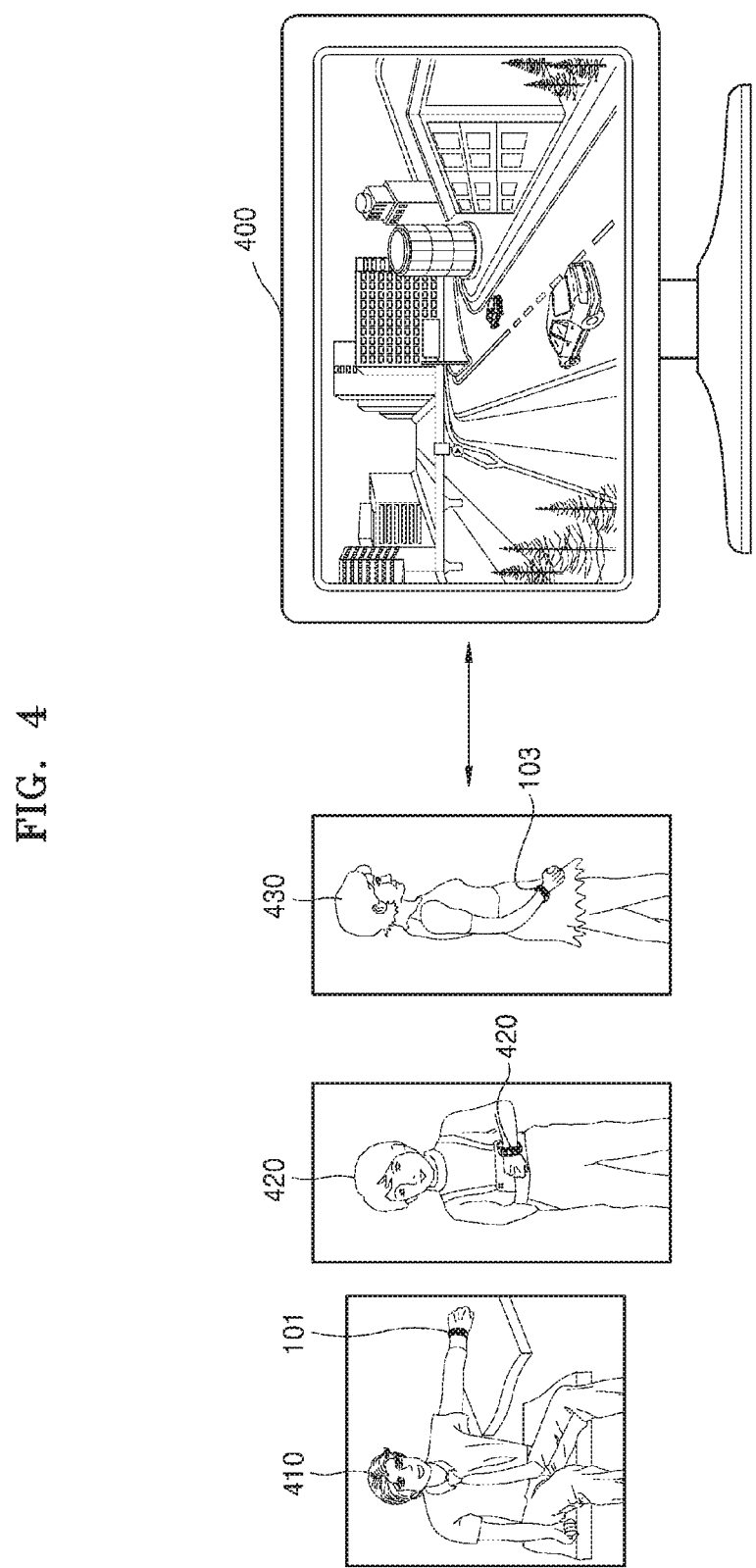

FIG. 6

| FIRST FIELD | SECOND FIELD | THIRD FIELD | FOURTH FIELD | ... | $n^{th}$ FIELD |

FIG. 7

| IDENTIFICATION INFORMATION | STATE INFORMATION | CONTROL INFORMATION | ... | $n^{th}$ FIELD |

FIG. 8

| APPROVAL INFORMATION | IDENTIFICATION INFORMATION | STATE INFORMATION | ENVIRONMENT INFORMATION | LOCATION INFORMATION | ... | $n^{th}$ FIELD |

DEVICE AND METHOD FOR TRANSMITTING MESSAGE

TECHNICAL FIELD

The present disclosure relates to a device and method of transmitting a message, and more particularly, to a device and method of transmitting a message obtained based on bio information of a user.

BACKGROUND ART

With developments in multimedia technology and data processing technology, devices have become able to process diverse pieces of information. In particular, a method of operating a device through an input by a user for controlling the device has been widely used. However, when the user controls the device, the user has to consciously transmit the input for controlling the device.

Therefore, a method of operating a device is required based on a situation of the user and without a direct input of the user.

DETAILED DESCRIPTION OF THE INVENTION

Technical Problem

Provided are a device and method of transmitting a message obtained based on bio information of a user.

Technical Solution

Provided is a method of transmitting a message. The method includes: obtaining identification information used to identify a user based on bio information of the user, wherein the bio information is obtained by the device; determining whether control over an external device is approved based on the identification information; obtaining control information used to control an operation of the external device based on the determining; and transmitting a message including the control information to the external device.

Advantageous Effects of the Invention

Provided is a method of operating a device based on a situation of a user and without a direct input of the user.

BRIEF DESCRIPTION OF THE DRAWINGS

FIG. 4 illustrates operations of devices according to an exemplary embodiment.

FIG. 6 illustrates an example of a structure of a message transmitted by a device, according to an exemplary embodiment.

FIG. 7 illustrates an example of a structure of a message transmitted by a device, according to another exemplary embodiment.

FIG. 8 illustrates an example of a structure of a message transmitted by a device, according to another exemplary embodiment.

BEST MODE

Figure 1:
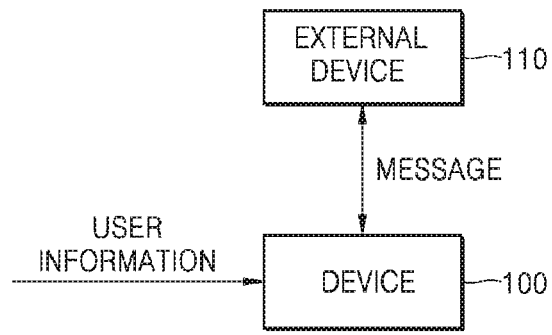
FIG. 1 illustrates an example, performed by a device, of receiving user information and transmitting a message, according to an exemplary embodiment.

According to an aspect of an exemplary embodiment, a method, performed by a device, of transmitting a message includes: obtaining identification information used to identify a user based on bio information of the user, wherein the bio information is obtained by the device; determining whether control over an external device is approved based on the identification information; obtaining control information used to control an operation of the external device based on the determining; and transmitting a message including the control information to the external device.

The obtaining of the control information may include: obtaining state information indicating a current state of the user based on the bio information; and obtaining the control information that is determined corresponding to the state information.

The obtaining of the control information may include obtaining the control information when it is determined that the control over the external device by the user is approved.

The message may further include the identification information and the state information.

The identification information may be stored in a predetermined first field of the message, the state information may be stored in a predetermined second field of the message, and the control information may be stored in a predetermined third field of the message.

The obtaining of the identification information may include obtaining the bio information by using a sensor included in the device.

The bio information may include at least one of fingerprint information, heartbeat information, iris information, vein information, palm pattern information, gait information, blood vessel information, body temperature information, electrocardiogram (ECG) information, blood pressure information, and location information.

The determining of whether the control over the external device is approved may include: determining an identification (ID) corresponding to the user based on the identification information; and determining whether the determined ID is included among one of more Ms that are allowed to control the external device.

The control information may include priority order information indicating an order of the control over the external device by a plurality of devices among which is included the device.

According to an aspect of an exemplary embodiment, a method of operating an external device includes: receiving a message including control information that is obtained based on bio information of a user who is allowed to control the external device and is used to control an operation of the external device; parsing the message; and performing an operation of showing the parsed message.

The control information may be obtained based on the bio information and/or state information indicating a current state of the user According to an aspect of another exemplary embodiment, a device includes: a bio information obtaining unit configured to obtain bio information from a user; a controller configured to obtain identification information used to identify the user based on the obtained bio information, determine whether control over an external device is approved based on the identification information, and obtain control information used to control an operation of the external device based on the determination; and a transmission unit configured to transmit a message including the control information to the external device.

The controller may be further configured to obtain state information indicating a current state of the user based on the bio information and obtain the control information determined corresponding to the state information.

The controller may be further configured to obtain the control information when it is determined that the control over the external device by the user is approved.

The message may further include the identification information and the state information.

The identification information may be stored in a predetermined first field of the message, the state information may be stored in a predetermined second field of the message, and the control information may be stored in a predetermined third field of the message.

According to an aspect of an exemplary embodiment, a sensor configured to obtain the bio information may be further included.

The bio information may include at least one of fingerprint information, heartbeat information, iris information, vein information, palm pattern information, gait information, blood vessel information, body temperature information, electrocardiogram (ECG) information, blood pressure information, and location information.

The controller may be further configured to determine an ID corresponding to the user based on the identification information and determine whether the determined ID is included among one or more IDs that are allowed to control the external device.

The control information may include priority order information indicating an order of the control over the external device by a plurality of devices among which is included the device.

According to an aspect of an exemplary embodiment, a non-transitory computer-readable recording medium has embodied thereon a computer program for performing the method of transmitting a message.

According to an aspect of an exemplary embodiment, there is provided a computer program stored in a non-transitory computer-readable recording medium to perform the method of transmitting a message.

MODE OF THE INVENTION

The attached drawings for illustrating exemplary embodiments of the present disclosure are referred to in order to gain a sufficient understanding of the present disclosure, the merits thereof, and the objectives accomplished by the implementation of the present disclosure. The present disclosure may, however, be embodied in many different forms and should not be construed as being limited to the embodiments set forth herein; rather, these embodiments are provided so that this disclosure will be thorough and complete, and will fully convey the concept of the present disclosure to those skilled in the art. The terms used therein will be briefly defined, and then exemplary embodiments will be described in detail.

The terms used in this specification are those general terms currently widely used in the art in consideration of functions regarding the inventive concept, but the terms may vary according to the intention of those of ordinary skill in the art, precedents, or new technology in the art. Also, specified terms may be selected by the applicant, and in this case, the detailed meaning thereof will be described in the detailed description of the inventive concept. Thus, the terms used in the specification should be understood not as simple names but based on the meaning of the terms and the overall description of the present disclosure.

It will be further understood that the terms "comprises" and/or "comprising" used herein specify the presence of stated features or components, but do not preclude the presence or addition of one or more other features or components. Also, the term "unit" used in the specification indicates a software component or a hardware component such as a field-programmable gate array (FPGA) or an application specific integrated circuit (ASIC), and the "unit" performs certain functions. However, the "unit" is not limited thereto. The "unit" may be configured to be included in a storage medium capable of performing addressing or configured to operate one or more processors. Therefore, the "unit" may include, for example, components such as software components, object-oriented software components, class components, and task components, processes, functions, properties, procedures, sub-routines, segments of program codes, drivers, firmware, micro codes, circuits, data, databases, data structures, tables, arrays, and variables. The components and "units" may be divided into additional components and "units" or may be a combination of a smaller number of components and "units".

Also, throughout the specification, the term "button input" may be an input of controlling, by a user, a device 100 by using a physical button attached to the device 100.

Also, throughout the specification, the term "gesture input" may be a gesture applied to the device 100 in order to transmit an input to the device 100. For example, the gesture input may include an input of rotating the device 100, tilting the device 100, or moving the device 100 vertically or horizontally. The device 100 may detect a predetermined gesture input of the user by using an acceleration sensor, a tilt sensor, a Gyro sensor, a 3-axis Magnetic sensor, or the like.

Hereinafter, the present disclosure will be described in detail by explaining exemplary embodiments of the present disclosure with reference to the attached drawings. For clarity, portions of drawings that are not related to the descriptions will be omitted.

FIG. 1 illustrates an example of receiving user information and transmitting a message by the device 100, according to an exemplary embodiment.

The device 100 may receive the user information. For example, the device 100 may receive bio information of a user. The bio information may include at least one of fingerprint information, heartbeat information, iris information, vein information, palm pattern information, gait information, blood vessel information, body temperature information, electrocardiogram (ECG) information, blood pressure information, and location information.

Alternatively, the bio information may include at least one of fingerprint information, heartbeat information, iris information, vein information, palm pattern information, and gait information.

The device 100 according to an exemplary embodiment may be wearable. For example, the device 100 may be embodied as a watch, glasses, earrings, a necklace, earphones, earring-type accessories, shoes, a ring, clothes, a helmet, or the like. However, the device 100 is not limited thereto and may be directly placed on a body part of the user. For example, the device 100 may be of a patch type or may be of a contact type or a non-contact type attached to or detached from a body part of the user. Also, the device 100 may be inserted into a body part of the user. For example, the device 100 may be embodied as epidermal electronics (or E-skin), an E-tattoo, or the like and thus may be inserted into epidermis or the body of the user through medical procedures.

Wearing the device 100 means that the user holds the device 100 such that the device 100 contacts a body part of the user. For example, the user may wear a watch, glasses, earrings, a necklace, earphones, shoes, a ring, clothes, or a helmet, or wear earring-type accessories over an external portion of an ear.

The device 100 may use Bluetooth and/or to receive/transmit data from/to the external device 110.

The device 100 may receive/transmit data from/to the external device 110. For example, the device 100 may receive/transmit a message from/to the external device 110.

The message transmitted by the device 100 to the external device 110 may be generated in a predetermined manner. A detailed form of the message will be described with reference to FIGS. 6 to 9.

The external device 110 may operate based on the message received from the device 100. For example, the external device 110 may be controlled based on control information included in the message.

The external device 110 may receive the message from the device 100.

The message may include the control information. A detailed form of the message will be described with reference to FIGS. 6 to 9.

The external device 110 may parse the message received from the device 100 and may perform an operation indicated by the parsed message.

The external device 110 may parse the message received from the device 100 so as to obtain bio information and may generate state information or control information by using the obtained bio information.

The control information may be obtained based on the bio information and/or the state information.

Figure 2:
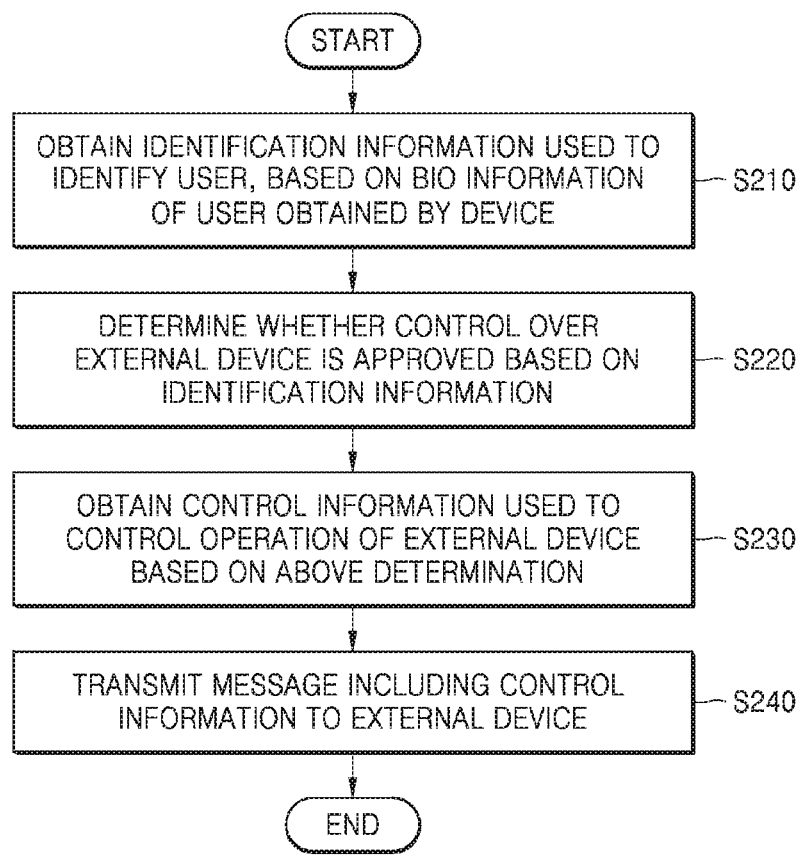
FIG. 2 illustrates a flowchart of a method, performed by a device, of transmitting a message according to an exemplary embodiment.

FIG. 2 illustrates a flowchart of a method of transmitting a message by the device 100 according to an exemplary embodiment.

In operation S210, the device 100 according to an exemplary embodiment may obtain identification information based on the obtained bio information of the user. The identification information may be information used to identify the user. For example, the device 100 may obtain fingerprint information of the user from the user of the device 100 and may obtain an identification (ID) corresponding to the obtained fingerprint information. As another example, the device 100 may obtain iris information of the user and may select an ID corresponding to the obtained iris information from among IDs stored in the device 100. As another example, the device 100 may obtain at least one of fingerprint information, heartbeat information, iris information, vein information, palm pattern information, gait information, blood vessel information, body temperature information, ECG information, blood pressure information, and location information and may obtain identification information corresponding to the at least one obtained information.

The device 100 according to an exemplary embodiment may obtain bio information by using a sensor included in the device 100. For example, the device 100 may obtain body temperature information by using a body temperature measuring sensor included in the device 100.

The device 100 according to another exemplary embodiment may obtain the bio information by receiving the bio information via wireless communication.

In operation S220, the device 100 may determine whether control over the external device 110 is approved based on the identification information obtained in operation S210.

For example, the device 100 may determine whether control over a television (TV) that is the external device 110 is approved by using the ID selected in operation S210. The ID that is allowed to control the external device 110 may be stored in the device 100.

As another example, when the external device 110 is a washing machine, the device 100 may determine whether an identified user is a user who is allowed to control the washing machine. For example, when the identified use is a child, the device 100 may determine that control over the external device 110 by the identified user is not approved. In this case, the ID corresponding to the child who is the identified user may not be included among IDs that are allowed to control the washing machine.

The device 100 may identify the user based on the identification information obtained in operation S220.

For example, the device 100 may determine the ID corresponding to the user based on the obtained identification information. The ID may be embodied in a predetermined manner. For example, the ID may be embodied as numbers, English letters, special characters, or a combination of numbers and English letters. The device 100 may select an ID corresponding to the obtained fingerprint information from among the IDs stored in the device 100.

As another example, the device 100 may obtain personal data corresponding to the identification information obtained in operation S220. For example, the device 100 may obtain a user ID corresponding to the obtained fingerprint information and obtain information regarding an interest corresponding to the obtained user ID from a server or a storage unit. The storage unit may be included in the device 100.

As another example, the device 100 may select one of the IDs registered in the device 100 by using the identification information obtained in operation S220. For example, the device 100 may select an ID corresponding to the obtained identification information from among a hundred IDs registered in the device 100. In this case, when the ID corresponding to the obtained identification information is not included among the registered IDs, the device 100 may not determine the identified user.

The device 100 may determine whether the identified user is included in an object that is allowed to control the external device 110.

Some of the users registered in the device 100 may be allowed to control the external device 110. For example, from among a first user, a second user, and a third user registered in the device 100, the first user and the second user are allowed to control the external device 110. In this case, the device 100 may determine whether the identified user is the first user or the second user.

As another example, the device 100 determines an ID corresponding to the obtained identification information and may determine whether the determined. ID is an ID that is allowed to control the external device 110.

For example, the device 100 may determine an ID corresponding to the obtained identification information as a seventh ID from among first to tenth IDs. The IDs that are allowed to control the external device 110 may be third to eighth IDs. In this case, the device 100 may determine the seventh ID that is the ID corresponding to the identification information as the ID that is allowed to control the external device 110.

The device 100 may register the user by using the bio information. For example, the device 100 may register the user by using at least one of fingerprint information, heartbeat information, iris information, vein information, palm pattern information, gait information, blood vessel information, body temperature information, ECG information, and blood pressure information. For example, the device 100 may generate an ID corresponding to the received heartbeat information and may store the generated ID in the device 100. In this case, when receiving the predetermined heartbeat information, the device 100 may match the received heartbeat information to the generated ID.

As another example, the device 100 may generate the ID corresponding to the received fingerprint information and may register the generated ID as an ID that is allowed to control the external device 110.

The device 100 may identify the user according to the bio information. The identification information according to an exemplary embodiment may include the bio information used to identify the user. The identification information according to another exemplary embodiment may include encoded bio information.

The identification information may be stored in the device 100. For example, the device 100 may obtain the identification information corresponding to the obtained bio information from data stored in the device 100.

The identification information according to another exemplary embodiment may be stored in the server. For example, the device 100 may obtain the identification information corresponding to the obtained bio information from the server.

The identification information according to another exemplary embodiment may be stored in the external device 110. For example, when the device 100 transmits the bio information to the external device 110, the external device 110 may obtain the identification information corresponding to the received bio information from data stored in the external device 110. When the bio information is transmitted from the device 100 to the external device 110, the bio information may be encoded for transmission.

The device 100 may determine whether a current user is a user who is allowed to control the external device 110. For example, the device 100 may determine whether the control over the external device 110 is approved, based on the identification information.

The device 100 may determine whether the control over the external device 110 is approved at a predetermined point in time.

For example, the device 100 may determine whether the control over the external device 110 by a current user is approved at a point in time when the user wears the device 100. The device 100 may use a sensor included in the device 100 in order to determine the point in time when the user wears the device 100. For example, the device 100 may determine whether the user wears the device 100 by using a body temperature detecting sensor included in the device 100.

As another example, the device 100 may determine whether the control over the external device 110 by the current user is approved at a point in time when the user is about to attempt to control the external device 110. The device 100 may determine the point in time in a predetermined manner. For example, the device 100 may determine a point in time when a predetermined button input is received as the point in time when the user is about to attempt to control the external device 110. As another example, the device 100 may determine a point in time when a predetermined gesture input is received as the point in time when the user is about to attempt to control the external device 110. As another example, the device 100 may determine a point in time when a user input of indicating a certain direction is received as the point in time when the user is about to attempt to control the external device 110.

As another example, the device 100 may determine a point in time when a determination as to whether the control over the external device 110 is approved is made, based on a location of the device 100. For example, when the device 100 is located within a predetermined distance from the external device 110, the device 100 may determine whether the control over the external device 110 by the current user is approved. As another example, when the device 100 is located at a predetermined location, the device 100 may determine whether the control over the external device 110 by the current user is approved.

In operation S230, the device 100 may obtain control information used to control an operation of the external device 110 based on the determination made in operation S220. For example, when it is determined that the control over the external device 110 by an identified user is approved, the device 100 may obtain or generate control information indicating a method of controlling the external device 110. As another example, when the identified user is not allowed to control the external device 110, the device 100 may not generate the control information indicating the method of controlling the external device 110.

The device 100 may obtain state information indicating a current state of the user based on bio information. For example, the device 100 may obtain state information indicating whether a body temperature of the user is high or low by using body temperature information that is the bio information. As another example, the device 100 may obtain information regarding a current psychological state of the user by using ECG information that is the bio information. As another example, the device 100 may obtain information indicating whether the user has a health problem by using blood vessel information that is the bio information.

The state information may include at least one of heart rate information, body temperature information, sweat amount information, blood pressure information, movement velocity information, and emotional state information. The emotional state information may include information indicating an emotional state of the user, for example, indicating whether the user is gloomy, angry, happy, etc. Also, the emotional state information may be obtained by using another piece of state information, for example, the heart rate information or body temperature information.

The device 100 may obtain control information determined corresponding to the obtained state information. For example, the device 100 may generate control information used to operate an air conditioner when the state information indicates that the body temperature of the user is high. As another example, the device 100 may generate control information used to make an audio device reproduce music that relaxes the user when the state information indicates that the user feels tense. As another example, when the state information indicates that the user has a health problem, the device 100 may generate control information used to make a TV display a screen for providing relevant knowledge. As another example, the device 100 may generate control information used to turn off light when the state information indicates that the user falls asleep. As another example, the device 100 may generate control information used to operate an air conditioner when the state information indicates that a current temperature is high. As another example, when the state information indicates that the user desires to manipulate a TV, the device 100 may generate control information used to make the TV display a channel preferable to the user by analyzing user information corresponding to current bio information.

The control information may include priority order information indicating an order of the control over the external device 110 by a plurality of devices among which is included the device 100. For example, when there are multiple devices generating control information regarding the external device 110, and when pieces of control information indicating performing of different operations are received from the devices, the external device 110 may perform an operation indicated by the control information of a device having a high priority from among the devices. For example, when a first device transmits, to the external device 110, a message including control information used to make the first device reproduce a first piece of music, and when a second device transmits, to the external device 110, a message including control information used to make the second device reproduce a second piece of music, the external device 110 may reproduce the first piece of music according to the message received from the first device having a higher priority than the second device. In this case, the control information generated by the first device may include priority order information indicating the priority of the first device. Also, the control information generated by the second device may include priority order information indicating the priority of the second device.

The external device 110 may operate based on the control information including the priority order information.

For example, if there are multiple devices and the first device has a higher priority than the second device with regard to control over a TV, when the control information generated by the first device indicates displaying a first channel, and the control information generated by the second device indicates displaying a second channel, the TV may be controlled to display the first channel. As another example, if there are multiple devices and the first device has a higher priority than the second device with regard to control over an air conditioner, when the control information generated by the first device may indicate an operation of the air conditioner and the control information generated by the second device may indicate stopping of the air conditioner, the air conditioner may be controlled to operate.

In operation S240, the device 100 may transmit, to the external device 110, the message including the control information obtained in operation S230.

The message according to an exemplary embodiment may include the control information.

A message according to another exemplary embodiment may include at least one of control information, identification information, state information, and bio information.

The message may store the control information, the identification information, the state information, and the bio information in predetermined fields of the message, respectively. For example, when the message has a first field, a second field, and a third field, and when each of the first to third fields corresponds to a predetermined data storage place of the message, the identification information is stored in the first field, the state information is stored in the second field, and the control information is stored in the third field.

A detailed form of the message will be described below with reference to FIGS. 6 to 9.

The device 100 may transmit the message at a predetermined point in time.

For example, the device 100 may periodically transmit the message to the external device 110 or the server. The device 100 may transmit the message once to the server at a predetermined time interval. For example, the device 100 may transmit the message to the server per every ten seconds.

As another example, when receiving a predetermined signal, the device 100 may transmit the message to the external device 110 or the server. For example, when it is determined that the user wears the device 100 by using a sensor included in the device 100, the device 100 may transmit the message to the external device 110. As another example, when it is determined that the user stops wearing the device 100 by using the sensor included in the device 100, the device 100 may transmit the message to the external device 110.

As another example, the device 100 may determine whether to transmit the message based on a location of the device 100. For example, when the device 100 is located in a predetermined distance from the external device 110, the device 100 may transmit the message to the external device 110.

As another example, when receiving a request for transmitting the message from the external device 110, the device 100 may transmit the message to the external device 110.

Figure 3:
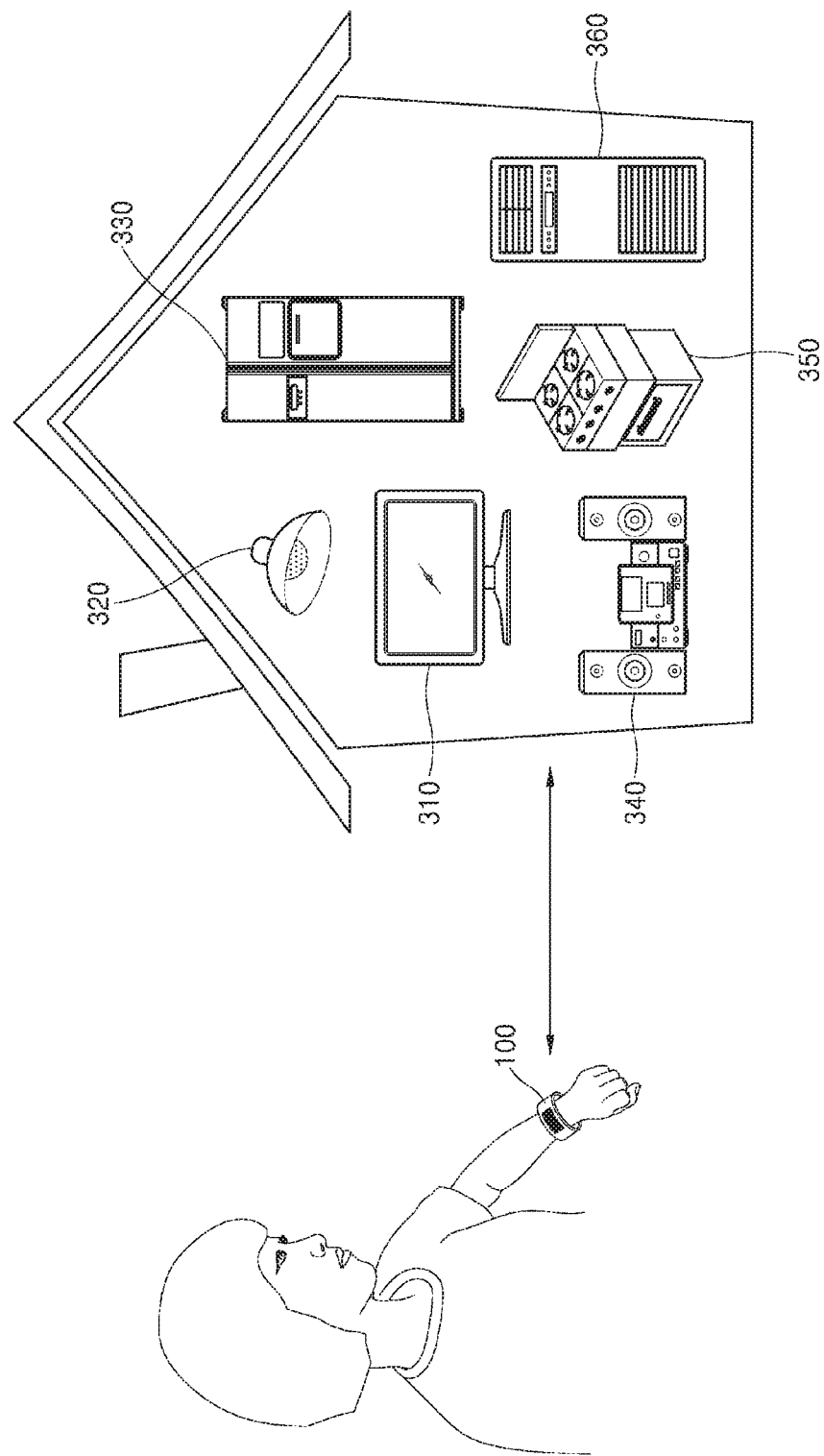
FIG. 3 illustrates an example, performed by a device, of transmitting a message in order to control an external device, according to an exemplary embodiment.

FIG. 3 illustrates an example of transmitting a message by the device 100 to control an external device, according to an exemplary embodiment.

The device 100 may control one or more external devices. For example, the device 100 may control at least one of a TV 310, a lamp 320, a refrigerator 330, an audio 340, a microwave 350, and an air conditioner 360.

The device 100 may be wearable or may not be wearable. For example, the device 100 may be a watch or a mobile phone.

FIG. 4 illustrates operations of controlling first to third devices 101, 102 and 103 according to an exemplary embodiment.

An external device 400 may be controlled by users 410, 420 and 430. For example, the external device 400 may be controlled by first to third devices 101, 102 and 103. The first device 101, the second device 102, and the third device 103 may control the external device 400. In this case, priorities corresponding to the first device 101, the second device 102, and the third device 103 may be assigned to the first device 101, the second device 102, and the third device 103, respectively. For example, if the first device 101 has the highest priority, when the first device 101, the second device 102, and the third device 103 transmit, to the external device 400, messages that request respectively performing different operations, the external device 400 may perform an operation indicated by the message received from the first device 101.

Figure 5A:
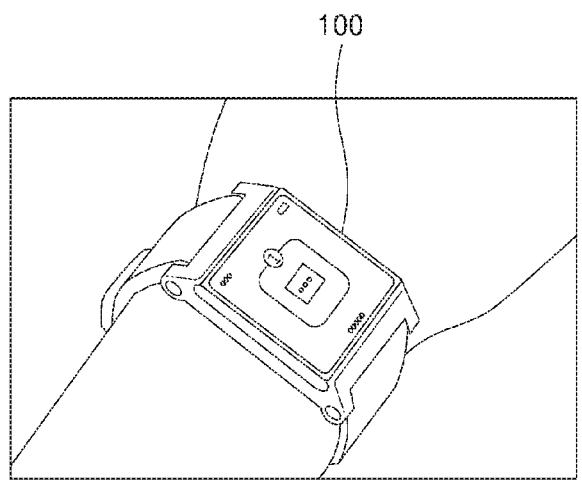
FIG. 5a illustrates an example of a device placed on a wrist of a user according to an exemplary embodiment.

FIG. 5*a* illustrates an example of the device 100 placed on a wrist of a user according to an exemplary embodiment.

The device 100 may obtain at least one of body temperature information, location information, vein information, gait information, and heartbeat information.

The device 100 may determine whether the user wears the device 100 by using the body temperature information.

Figure 5B:
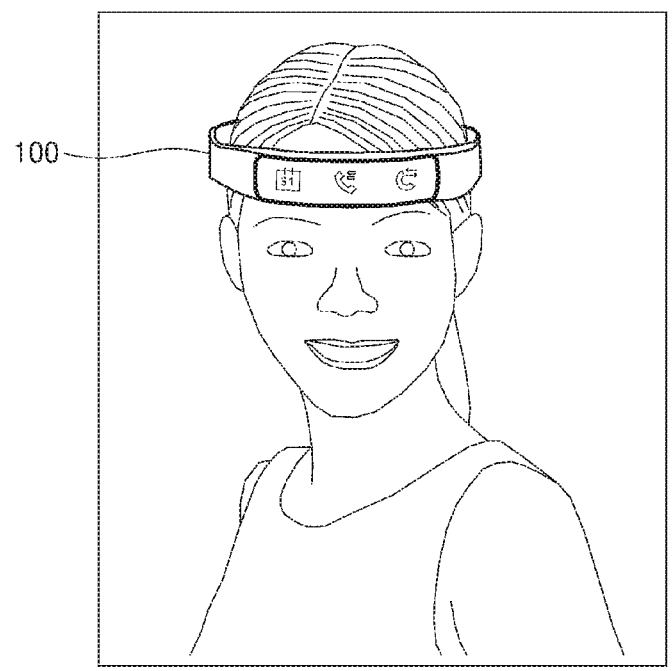
FIG. 5b illustrates an example of a device placed on a head of a user according to an exemplary embodiment.

FIG. 5*b* illustrates an example of the device 100 placed on a head of a user according to an exemplary embodiment.

The device 100 may obtain at least one of heartbeat information, vein information, blood vessel information, body temperature information, ECG information, blood pressure information, and location information.

The device 100 determines whether the user sleeps, a message controlling the external device 110 may be transmitted according to whether the user sleeps.

Figure 5C:
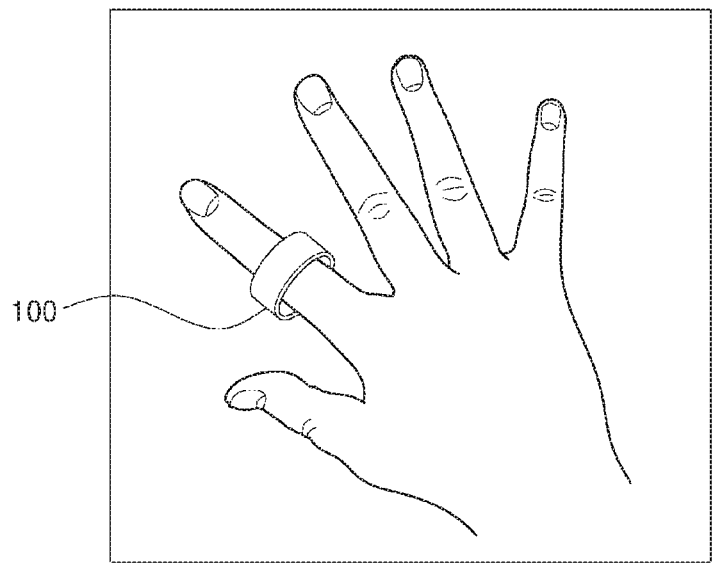
FIG. 5c illustrates an example of a device placed on a finger of a user according to an exemplary embodiment.

FIG. 5*c* illustrates an example of the device 100 placed on a finger of a user according to an exemplary embodiment.

The device 100 may obtain at least one of heartbeat information, vein information, gait information, blood vessel information, body temperature information, ECG information, blood pressure information, and location information.

The device 100 may obtain a finger gesture and may transmit a message controlling the external device 110 to the external device 110 according to the obtained finger gesture.

Figure 5D:
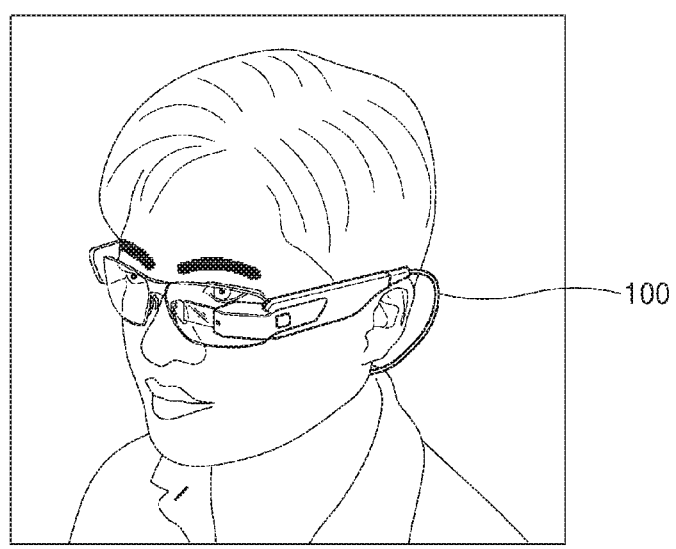
FIG. 5d illustrates an example of a device placed on a face of a user according to an exemplary embodiment.

FIG. 5*d* illustrates an example of the device 100 placed on a face of a user according to an exemplary embodiment.

The device 100 may obtain at least one of heartbeat information, iris information, vein information, gait information, blood vessel information, body temperature information, ECG information, blood pressure information, and location information.

The device 100 may obtain a gesture of blinking eyes of the user and may transmit a message controlling the external device 110 to the external device 110 according to the obtained gesture.

Figure 5E:
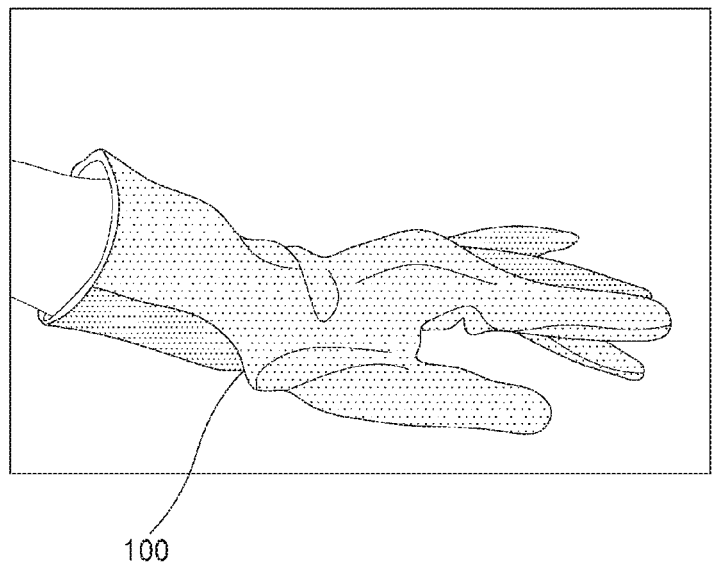
FIG. 5e illustrates an example of a device placed on a hand of a user according to an exemplary embodiment.

FIG. 5*e* illustrates an example of the device 100 placed on a hand of a user according to an exemplary embodiment.

The device 100 may obtain at least one of fingerprint information, heartbeat information, vein information, palm pattern information, gait information, blood vessel information, body temperature information, ECG information, blood pressure information, and location information.

The device 100 obtains a hand gesture and may transmit a message controlling the external device 110 to the external device 110 according to the obtained hand gesture.

FIG. 6 illustrates an example of a structure of a message transmitted by the device 100, according to an exemplary embodiment.

The message may be expressed as a data stream. The message may include a plurality of fields. Predetermined types of pieces of data may be recorded in each field. For example, identification information may be recorded in a first field.

The fields included in the message may be predetermined. For example, a data storage space assigned to the first field may be predetermined to have a capacity of 8 bytes.

The message may include the determined number of fields. A predetermined data storage space may be assigned to each field included in the message.

FIG. 7 illustrates an example of a structure of a message transmitted by the device 100, according to another exemplary embodiment.

The message may include control information.

The message may include at least one of identification information, state information, and control information. For example, the identification information may be recorded in a first field placed in front of the message. As another example, the identification information may be recorded in the first field, the state information may be recorded in a second field, and the control information may be recorded in a third field.

When a message according to another exemplary embodiment only includes the state information, the external device 110 may receive a message from the device 100 and may generate the control information based on the state information.

When a message according to another exemplary embodiment includes the control information, the external device 110 may receive a message from the device 100 and may perform an operation based on the control information.

FIG. 8 illustrates an example of a structure of a message transmitted by the device 100, according to another exemplary embodiment.

The message may not include control information.

The message may include at least one of identification information, state information, environment information, and location information.

For example, approval information may be recorded in a first field of the message. The approval information may be information indicating whether the control over the external device 110 is approved.

As another example, the identification information may be recorded in a second field of the message. The external device 110 may identify the device 100 transmitting the message from among the devices, based on the identification information.

As another example, the state information may be recorded in a third field of the message. The external device 110 may generate control information based on the state information. For example, the external device 110 may determine operations to be performed by the external device 110 based on the state information. For example, when the external device 110 is an air conditioner, and when the state information indicates that a room temperature is high, the external device 110 may operate to decrease the room temperature.

As another example, the environment information may be recorded in a fourth field of the message. The environment information may be information regarding a neighboring environment of the device 100. For example, the environment information may include at least one of temperature information, humidity information, illumination information, fine dust information, smell information, atmospheric pressure information, and time information. As another example, the environment information may include information regarding a temperature or climate around the device 100. As another example, the environment information may include time zone information about a time zone in an area where the device 100 is located. The external device 110 may generate the control information or may determine an operation to be performed by the external device 110. For example, when it rains, the external device 110 may perform an operation of removing humidity, based on the environment information.

As another example, location information may be recorded in a fifth field of the message. The location information may indicate information about a location of the device 100. For example, the location information may indicate location information about a current location of the device 100. As another example, the location information may include information about a distance between the external device 110 and the device 100. The external device 110 may generate the control information or may determine an operation to be performed by the external device 110, based on the location information. For example, the external device 110 may perform a predetermined operation when the device 100 is located within a predetermined distance from the external device 110.

Figure 9:
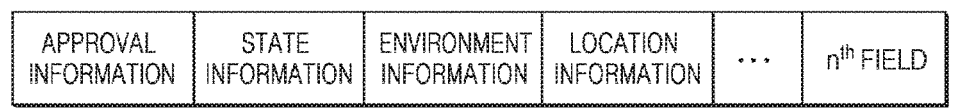
FIG. 9 illustrates an example of a structure of a message transmitted by a device, according to another exemplary embodiment.

FIG. 9 illustrates an example of a structure of a message transmitted by the device 100, according to another exemplary embodiment.

The message may include bio information.

When the message includes the bio information, the external device 110 may receive a message from the device 100 and may generate state information and control information based on the received message.

The message may include at least one of bio information, state information, environment information, and location information.

For example, the bio information may be recorded in a first field of the message. The bio information may be information regarding a body part that is obtained by the device 100. The external device 110 may generate the identification information or the control information based on the bio information. For example, the external device 110 may generate the identification information based on fingerprint information. As another example, the external device 110 may generate control information indicating a decrease of a room temperature, based on the bio information indicating a high temperature.

As another example, the state information may be recorded in a second field of the message.

As another example, the environment information may be recorded in a third field of the message.

As another example, location information may be recorded in a fourth field of the message.

Figure 10:
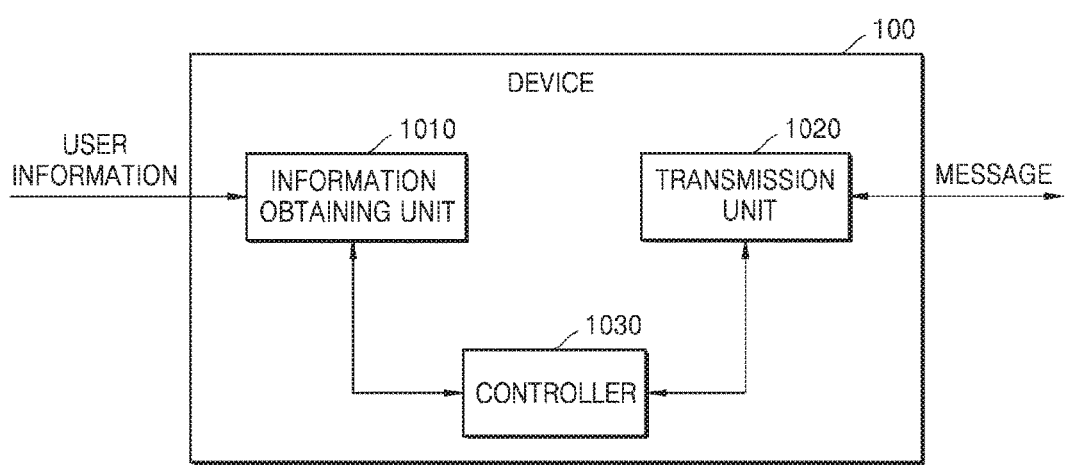
FIG. 10 illustrates a block diagram of a structure of a device according to an exemplary embodiment.
Figure 11:
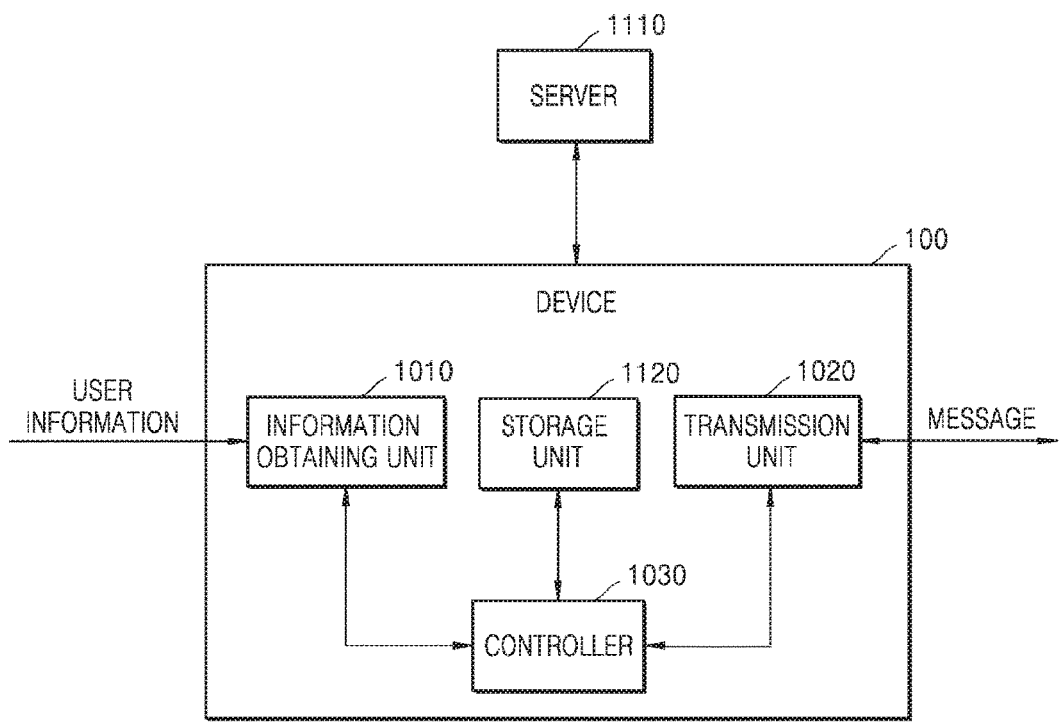
FIG. 11 illustrates a block diagram of a structure of a device according to another exemplary embodiment.

FIGS. 10 and 11 illustrate the device 100 according to one or more exemplary embodiments. The device 100 may perform the above-described method of transmitting the message and may implement one or more exemplary embodiments for performing the above-described method.

FIG. 10 illustrates a block diagram of a structure of the device 100 according to an exemplary embodiment.

As described with reference to FIG. 10, the device 100 may include an information obtaining unit 1010, a transmission unit 1020, and a controller 1030. The device 100 may be embodied by more or less components than the illustrated component.

The components will be described below.

The information obtaining unit 1010 may obtain user information from the outside of the device 100. For example, the information obtaining unit 1010 may obtain bio signals. The bio information may include at least one of fingerprint information, heartbeat information, iris information, vein information, palm pattern information, gait information, blood vessel information, body temperature information, ECG information, blood pressure information, and location information.

The information obtaining unit 1010 may obtain the bio information by using a sensor included in the information obtaining unit 1010. For example, the information obtaining unit 1010 may obtain the body temperature information by using a body temperature measuring sensor included in the information obtaining unit 1010.

The information obtaining unit 1010 according to another exemplary embodiment may obtain the bio information by receiving the bio information via wireless communication.

The controller 1030 may obtain the identification information based on the obtained bio information of the user. The identification information may be information used to identify the user. For example, the information obtaining unit 1010 may obtain the fingerprint information of the user from the user of the device 100, and the controller 1030 may obtain an ID corresponding to the obtained fingerprint information. As another example, the information obtaining unit 1010 obtains iris information of the user, and the controller 1030 may select an ID corresponding to the obtained iris information from among IDs stored in the device 100. As another example, the information obtaining unit 1010 may obtain at least one of fingerprint information, heartbeat information, iris information, vein information, palm pattern information, gait information, blood vessel information, body temperature information, ECG information, blood pressure information, and location information of the user of the device 100, and the controller 130 may obtain the identification information corresponding to the obtained information.

The controller 1030 may determine whether the control over the external device 110 is approved, based on the obtained identification information.

For example, the controller 1030 may determine whether control of a TV that is the external device 110 is approved by using the selected ID. The ID that is allowed to control the external device 110 may be stored by the device 100.

As another example, when the external device 110 is a washing machine, the controller 1030 may determine whether the identified user is a user who is allowed to control the washing machine. For example, when the identified user is a child, the controller 1030 may determine that the control over the washing machine that is the external device 110 by the identified user is not approved. In this case, an ID corresponding to the child, which is the identified user, may not be included among IDs that are allowed to control the washing machine.

The controller 1030 may identify the user based on the obtained identification information.

For example, the controller 1030 may determine an ID corresponding to the user based on the obtained identification information. The ID may be embodied according to a predetermined method. For example, the ID may be embodied as numbers, alphabets, special characters, or a combination thereof. The controller 1030 may determine an ID corresponding to the obtained fingerprint information from among IDs stored in the device 100.

As another example, the controller 1030 may obtain personal data corresponding to the obtained identification information. For example, the controller 1030 obtains a user ID corresponding to the obtained fingerprint information and may obtain information regarding an interest corresponding to the obtained user ID from a server or a storage unit. The storage unit may be included in the device 100.

As another example, the controller 1030 may determine one of the IDs registered in the device 100 by using the obtained identification information. For example, the controller 1030 may determine an ID corresponding to the obtained identification information from among a hundred IDs registered in the device 100. In this case, when the ID corresponding to the obtained identification information does not exist among the IDs registered in the device 100, the controller 1030 may not determine an identified user.

The controller 1030 may determine the identified user is included in an object that is allowed to control the external device 110.

Some of the users registered in the device 100 may be allowed to control the external device 110. For example, from among a first user, a second user, and a third user registered in the device 100, the first user and the second user are allowed to control the external device 110. In this case, the device 100 may determine whether the identified user is the first user or the second user.

As another example, the controller 1030 determines an ID corresponding to the identification information and may determine whether the determined ID is an ID that is allowed to control the external device.

For example, the device 100 may determine an ID corresponding to the obtained identification information as a seventh ID from among first to tenth IDs. The IDs that are allowed to control the external device 110 may be third to eighth IDs. In this case, the device 100 may determine the seventh ID that is the ID corresponding to the identification information as the ID that is allowed to control the external device 110.

The controller 1030 may register a user by using the bio information. For example, the controller 1030 may register the user by using at least one of fingerprint information, heartbeat information, iris information, vein information, palm pattern information, gait information, blood vessel information, body temperature information, ECG information, and blood pressure information. For example, the controller 1030 may generate the ID corresponding to the received heartbeat information and store the generated ID in the device 100. In this case, when receiving the predetermined information, the controller 1030 may match the generated ID to the received heartbeat information.

As another example, the controller 1030 may generate the ID corresponding to the received fingerprint information and may register the generated ID as an ID that is allowed to control the external.

The controller 1030 may identify the user according to the bio information. The identification information may include the bio information used to identify the user. The identification information may include encoded bio information.

The identification information may be stored in the device 100. For example, the controller 1030 may obtain identification information corresponding to the obtained bio information from the data stored in the device 100.

The identification information may be stored in the server. For example, the controller 1030 may obtain the identification information corresponding to the obtained bio information from the server.

The identification information may be stored in the external device 110. For example, when the device 100 transmits the bio information to the external device 110, the external device 110 may obtain identification information corresponding to the received bio information from the data stored in the external device 110. When the bio information is transmitted from the device 100 to the external device 110, the bio information may be encoded for transmission.

The controller 1030 may determine whether a current user is a user who is allowed to control the external device 110. For example, the controller 1030 may determine whether the control over the external device 110 is approved, based on the identification information.

The controller 1030 may determine whether the control over the external device 110 is approved at a predetermined point in time.

For example, the controller 1030 may determine whether the control over the external device 110 by the current user is approved at a point in time when the user wears the device 100. The controller 1030 may use a sensor included in the device 100 in order to determine the point in time when the user wears the device 100. For example, the controller 1030 may determine whether the user wears the device 100 by using a body temperature detecting sensor included in the device 100.

As another example, the controller 1030 may determine whether the control over the external device 110 by the current user is approved at a point in time when the user is about to attempt to control the external device 110. The controller 1030 may determine the point in time in a predetermined manner. For example, the controller 1030 may determine a point in time when a predetermined button input is received as the point in time when the user is about to attempt to control the external device 110. As another example, the controller 1030 may determine a point in time when a predetermined gesture input is received as the point in time when the user is about to attempt to control the external device 110. As another example, the controller 1030 may determine a point in time when a user input of indicating a certain direction is received as the point in time when the user is about to attempt to control the external device 110.

As another example, the controller 1030 may determine a point in time when a determination as to whether the control over the external device 110 is approved is made, based on a location of the device 100. For example, when the device 100 is located within a predetermined distance from the external device 110, the controller 1030 may determine whether the control over the external device 110 by the current user is approved. As another example, when the device 100 is located at a predetermined location, the controller 1030 may determine whether the control over the external device 110 by the current user is approved.

The controller 1030 may obtain control information used to control an operation of the external device 110. For example, when it is determined that the control over the external device 110 by an identified user is approved, the controller 1030 may obtain or generate control information indicating a method of controlling the external device 110. As another example, when the identified user is not allowed to control the external device 110, the controller 1030 may not generate the control information indicating the method of controlling the external device 110.

The controller 1030 may obtain state information indicating a current state of the user based on bio information. For example, the controller 1030 may obtain state information indicating whether a body temperature of the user is high or low by using body temperature information that is the bio information. As another example, the controller 1030 may obtain information regarding a current psychological state of the user by using ECG information that is the bio information. As another example, the controller 1030 may obtain information indicating whether the user has a health problem by using blood vessel information that is the bio information.

The controller 1030 may obtain control information determined corresponding to the obtained state information. For example, the controller 1030 may generate control information used to operate an air conditioner when the state information indicates that the body temperature of the user is high. As another example, the controller 1030 may generate control information used to make an audio reproduce music that relaxes the user when the state information indicates that the user feels tense. As another example, when the state information indicates that the user has a health problem, the controller 1030 may generate control information used to make a TV display a screen for providing relevant knowledge. As another example, the controller 1030 may generate control information used to turn off light when the state information indicates that the user falls asleep. As another example, the controller 1030 may generate control information used to operate an air conditioner when the state information indicates that a current temperature is high. As another example, when the state information indicates that the user desires to manipulate a TV, the controller 1030 may generate control information used to make the TV display a channel preferable to the user by analyzing user information corresponding to current bio information.

The control information may include priority order information indicating an order of the control over the external device 110 by a plurality of devices among which is included the device 100. For example, when there are multiple devices generating control information regarding the external device 110, and when pieces of control information indicating performing of different operations are received from the devices, the external device 110 may perform an operation indicated by the control information of a device having a high priority from among the devices. For example, when a first device transmits, to the external device 110, a message including control information used to make the first device reproduce a first piece of music, and when a second device transmits, to the external device 110, a message including control information used to make the second device reproduce a second piece of music, the external device 110 may reproduce the first piece of music according to the message received from the first device having a higher priority than the second device. In this case, the control information generated by the first device may include priority order information indicating the priority of the first device. Also, the control information generated by the second device may include priority order information indicating the priority of the second device.

The external device 110 may operate based on the control information including the priority order information.

For example, if there are multiple devices and the first device has a higher priority than the second device with regard to control over a TV, when the control information generated by the first device may indicate displaying a first channel, and the control information generated by the second device may indicate displaying a second channel, the TV may be controlled to display the first channel. As another example, if there are multiple devices and the first device has a higher priority than the second device with regard to control over an air conditioner, when the control information generated by the first device may indicate an operation of the air conditioner and the control information generated by the second device may indicate stopping of the air conditioner, the air conditioner may be controlled to operate.

The transmission unit 1020 may transmit, to the external device 110, the message including the control information obtained by the controller 1030.

The message according to an exemplary embodiment may include the control information.

A message according to another exemplary embodiment may include at least one of control information, identification information, state information, and bio information.

The message may store the control information, the identification information, the state information, and the bio information in predetermined fields of the message, respectively. For example, when the message has a first field, a second field, and a third field, and when each of the first to third fields corresponds to a predetermined data storage place of the message, the identification information is stored in the first field, the state information is stored in the second field, and the control information is stored in the third field.

The device 100 may transmit the message at a predetermined point in time,

For example, the transmission unit 1020 may periodically transmit the message to the external device 110 or the server. The transmission unit 1020 may transmit the message once to the server at a predetermined time interval. For example, the transmission unit 1020 may transmit the message to the server per every ten seconds.

As another example, when receiving a predetermined signal, the transmission unit 1020 may transmit the message to the external device 110 or the server. For example, when it is determined that the user wears the device 100 by using a sensor included in the device 100, the transmission unit 1020 may transmit the message to the external device 110. As another example, when it is determined that the user stops wearing the device 100 by using the sensor included in the device 100, the transmission unit 1020 may transmit the message to the external device 110.

As another example, the transmission unit 1020 may determine whether to transmit the message based on a location of the device 100. For example, when the device 100 is located within a predetermined distance from the external device 110, the transmission unit 1020 may transmit the message to the external device 110.

As another example, when receiving a request for transmitting the message from the external device 110, the transmission unit 1020 may transmit the message to the external device 110.

FIG. 11 illustrates a block diagram of a structure of the device 100 according to another exemplary embodiment.

The device 100 may further include a storage unit 1120. Also, the device 100 may interwork the server 1110.

The operations of the storage unit 1120 and the server 1110 are described with reference to FIGS. 2 and 10, and thus, detailed descriptions thereof will be omitted.

Some exemplary embodiments may be embodied as a non-transitory computer-readable medium, for example, a program module executable by a computer, including commands executable by a computer. The non-transitory computer-readable medium may be an arbitrary medium accessed by a computer and includes a volatile/non-volatile medium and a removable medium. Also, the non-transitory computer-readable medium may include a storage medium and a communication medium. The storage medium includes a computer-readable command, a data structure, a program module, a volatile/non-volatile medium, or a removable medium, the volatile/non-volatile medium, and a removable medium embodied by an arbitrary method or technology of storing information such as data. The communication medium includes a computer-readable command, a data structure, a program module, data of a modulated data signal, or another transmission mechanism and also includes an arbitrary information transmission medium.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

The invention claimed is:

1. A method, performed by a device, of transmitting a message, the method comprising:
   obtaining identification information used to identify a user based on bio information of the user, wherein the bio information is obtained by the device;
   determining whether control over an external device is approved based on the identification information;
   obtaining control information used to control an operation of the external device based on the determining; and
   transmitting a message comprising the control information to the external device,
   wherein the identification information is stored in a predetermined first field of the message, state information indicating a current state of the user based on the bio information is stored in a predetermined second field of the message, and the control information determined corresponding to the state information is stored in a predetermined third field of the message.

2. The method of claim 1, wherein the obtaining of the control information comprises obtaining the control information when it is determined that the control over the external device by the user is approved.

3. The method of claim 1, wherein the obtaining of the identification information comprises obtaining the bio information by using a sensor included in the device.

4. The method of claim 1, wherein the bio information comprises at least one of fingerprint information, heartbeat information, iris information, vein information, palm pattern information, gait information, blood vessel information, body temperature information, electrocardiogram (ECG) information, blood pressure information, and location information.

5. The method of claim 1, wherein the determining of whether the control over the external device is approved comprises:
   determining an identification (ID) corresponding to the user based on the identification information; and
   determining whether the determined ID is included among one or more IDs that are allowed to control the external device.

6. The method of claim 1, wherein the control information comprises priority order information indicating an order of the control over the external device by a plurality of devices among which is included the device.

7. A device comprising:
   a sensor obtaining bio information from a user;
   at least one processor configured to:
      obtain identification information used to identify the user based on the obtained bio information,
      determine whether control over an external device is approved based on the identification information, and
      obtain control information used to control an operation of the external device based on the determination; and
   a transmitter for transmitting a message comprising the control information to the external device,
   wherein the identification information is stored in a predetermined first field of the message, state information indicating a current state of the user based on the bio information is stored in a predetermined second field of the message, and the control information determined corresponding to the state information is stored in a predetermined third field of the message.

8. The device of claim 7, wherein the at least one processor is further configured to obtain the control information when it is determined that the control over the external device by the user is approved.

9. The device of claim 7, further comprising a sensor configured to obtain the bio information.

10. The device of claim 7, wherein the bio information comprises at least one of fingerprint information, heartbeat information, iris information, vein information, palm pattern information, gait information, blood vessel information, body temperature information, electrocardiogram (ECG) information, blood pressure information, and location information.

11. The device of claim 7, wherein the at least one processor is further configured to:
   determine an identification (ID) corresponding to the user based on the identification information, and
   determine whether the determined ID is included among one or more IDs that are allowed to control the external device.

12. The device of claim 7, wherein the control information comprises priority order information indicating an order of the control over the external device by a plurality of devices among which is included the device.

13. A non-transitory computer-readable recording medium having recorded thereon a computer program, which, when executed by a computer, performs a method of transmitting a message by a device, the method comprising:
   obtaining identification information used to identify a user based on bio information of the user, wherein the bio information is obtained by the device;
   determining whether control over an external device is approved based on the identification information;
   obtaining control information used to control an operation of the external device based on the determining; and
   transmitting a message comprising the control information to the external device,
   wherein the identification information is stored in a predetermined first field of the message, state information indicating a current state of the user based on the bio information is stored in a predetermined second field of the message, and the control information determined corresponding to the state information is stored in a predetermined third field of the message.

14. A computer-program product comprising a non-transitory computer-readable storage medium having instructions for:
   obtaining identification information used to identify a user based on bio information of the user, wherein the bio information is obtained by the device;
   determining whether control over an external device is approved based on the identification information;
   obtaining control information used to control an operation of the external device based on the determining; and
   transmitting a message comprising the control information to the external device,
   wherein the identification information is stored in a predetermined first field of the message, state information indicating a current state of the user based on the bio information is stored in a predetermined second field of the message, and the control information determined corresponding to the state information is stored in a predetermined third field of the message.

* * * * *